United States Patent [19]

Hounsfield

[11] 3,934,142
[45] Jan. 20, 1976

[54] RADIOGRAPHY
[75] Inventor: Godfrey Newbold Hounsfield, Newark, England
[73] Assignee: E M I Limited, Hayes, England
[22] Filed: July 17, 1974
[21] Appl. No.: 489,084

[30] Foreign Application Priority Data
July 21, 1973 United Kingdom............... 34859/73

[52] U.S. Cl.............. 250/360; 250/366; 250/445 T; 250/514
[51] Int. Cl.² ........................................ G03B 41/16
[58] Field of Search ........... 250/514, 505, 439, 444, 250/445, 445 T, 446, 447, 451, 454, 456, 521, 358, 359, 360, 361, 362, 363, 366, 367, 368

[56] References Cited
UNITED STATES PATENTS
3,778,614  12/1973  Hounsfield.......................... 250/362

Primary Examiner—Craig E. Church
Attorney, Agent, or Firm—Fleit & Jacobson

[57] ABSTRACT

Radiographic apparatus is described in which a thin planar slice of the body is examined by a swath of penetrating radiation such as X-rays. Collimators are provided for collimating the radiation after it has passed through the body into a set of beams which are directed into respective detectors. The swath of radiation, the collimeters and the detectors are orbited in the plane of the slice so that the beams pass through the body from many different angular directions. Means are provided for additionally displacing at least the collimators relative to the source so that the relative position of the beams and gaps between the beams are changed during the orbital movement.

8 Claims, 1 Drawing Figure

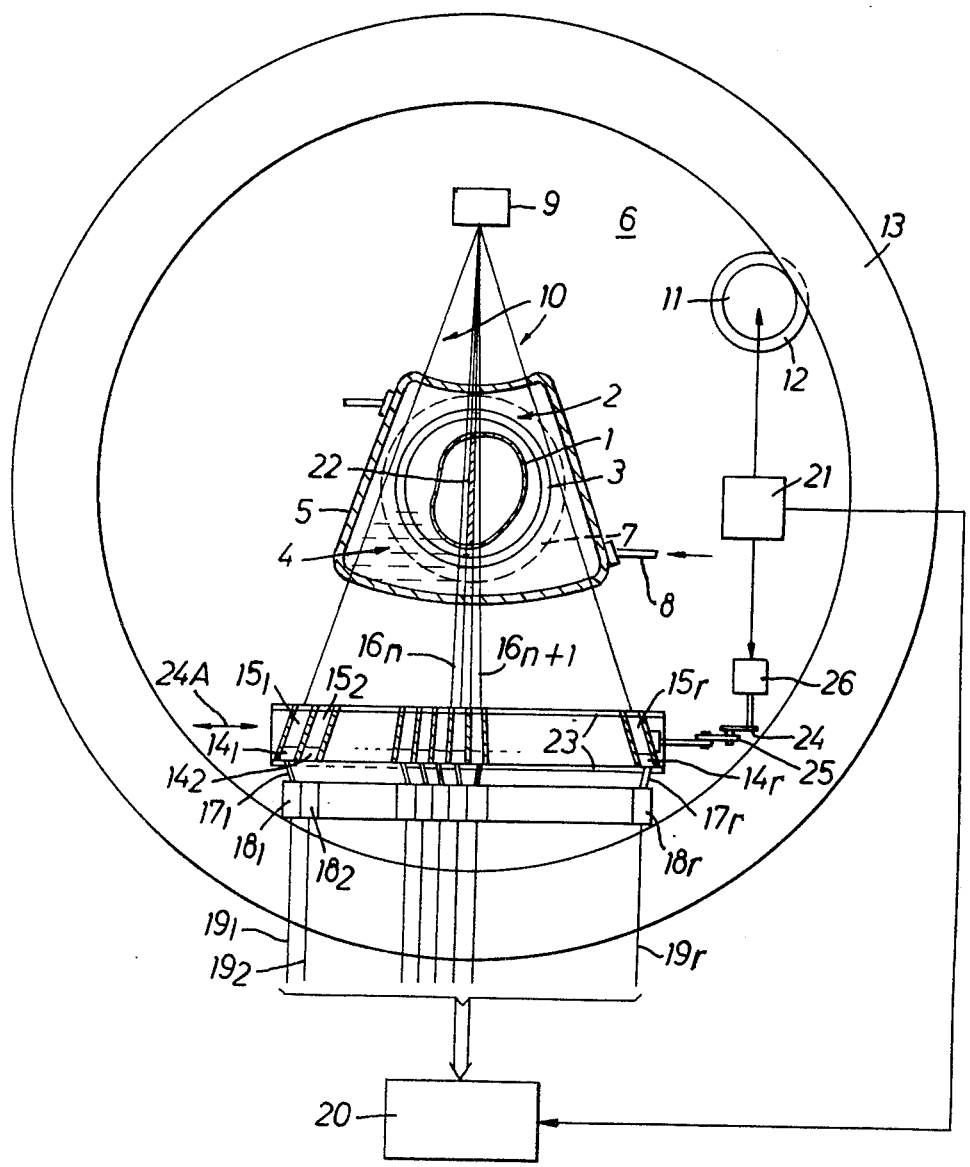

RADIOGRAPHY

The present invention relates to radiography, and it relates in particular to apparatus for examining a thin planar slice or section of a body.

In our British Patent Specification No. 1,283,915 there is described apparatus for examining a thin planar slice of the human body. In one form of the apparatus a source of X-radiation produces a collimated beam which is directed through the body to a detector disposed at the other side of the body from the source. Scanning movements are imparted to the source and detector which are such that the beam executes successive traverses at right angles to its length, so that the beam sweeps through the slice under examination. After each such traverse, the source and detector are rotated through a small angle, say, 1°, so that the successive traverse occurs with the beam in different angular dispositions. The output of the detector is sampled during each traverse so that successive output signals are obtained dependent on the transmissions of the beam through a succession of narrow paths which during any one traverse are parallel to one another. The sampling is carried out so that the signals derived during any one traverse are dependent on the transmission or absorption of all elements of the body in the planar slice swept by the beam during the particular traverse. From the many sets of output signals thus obtained, corresponding to sets of parallel beam paths, disposed at different angular orientations, a reconstruction of the absorption or transmission of the elements in the planar slice is produced. The scanning procedure outlined above is however relatively slow, and for the examination of parts of the body which move due to heart beats or breathing, a faster scanning techinque is required. With a view to providing such a technique it has been proposed to irradiate the entire slice under examination with a swath of radiation and to detect the transmission along narrow beams in the swath by means of a bank of collimated detectors, each detector thus providing the output of a single beam. With such an arrangement, the lateral scanning traverses can be dispensed with and the scanning can be effected by a continuation orbital movement of the source and the detectors. However, the need to provide a bank of detectors with associated collimators has the disadvantage that gaps are left between the adjacent beams. This means either that each set of output signals may include fewer than the desired number, or that narrower beams have to be used, reducing the signal to noise ratio of the signals.

The object of the present invention is to reduce this disadvantage.

According to the present invention there is provided radiographic apparatus comprising a source of penetrating radiation arranged to project a swath of radiation across a space for location of a body to be examined, means for collimating the radiation into a set of beams with gaps between adjacent beams, detector means for detecting the respective beams and for producing output signals dependent on the radiation transmitted in said beams, means for orbiting said source, said collimating means, and said detector means in the plane of said swath, and means for additionally displacing at least said collimating means relative to the source so that the relative positions of the beams and the gaps are changed during the orbital movement.

In order that the present invention may be clearly understood and readily carried into effect, one embodiment thereof will now be described with reference to the accompanying drawing, the single FIGURE of which shows, in schematic view, one example of apparatus in accordance with the present invention.

Referring to the drawing, a body to be examined is located in a short flexible hose 1, which forms one wall of a water reservoir 2, the hose being shown in section on the drawing. The hose 1, made of rubber, for example, is attached at each end to a rigid ring secured to the frame of the apparatus, one of these rings being denoted by the reference 3. The hose 1 is of sufficient size to allow the body of a patient to be examined to be inserted through the hose, so that the hose surrounds the abdomen for example. The other walls the reservoir 2, namely the end walls, one of which is shown at 4, and the outer wall 5, shown in section, are secured to a turntable 6, and to ensure that the reservoir is watertight, watertight seals, one of which is denoted at 7, are provided between the end rings 3 of the hose and the end walls 4 of the reservoir. After the body has been located within the hose 1, water is pumped into the reservoir by inlet 8, until the hose fits snugly around the patient, extruding air from between the patient and the hose. The walls 4 and 5 of the reservoir 2 are constructed of a plastics material which is substantially transparent to the radiation which is to be used in examining the body.

A source 9 of penetrating radiation such as X- or $\gamma$-radiation is arranged to produce a substantially planar sectoral swath 10 of the radiation and is mounted on the turntable 6. It will be observed that the path lengths for all rays on the swath 10 through the reservoir are substantially equal though part of the paths for some rays will be through the body, not through the water. The source 9 can be orbited around the body in the plane of the swath by rotation of the turntable 6, which can be effected by means of an electrical motor 11 which drives a gear wheel 12 engaging with gear teeth (not shown) provided all around the inner periphery of a stationary member 13. This member 13 is part of the frame of the apparatus to which the rings 3 are attached. As the outer wall 5 of the reservoir 2 is attached to the turntable, it rotates with it, and always presents the same profile to the swath 10.

A bank of radiation sensitive crystals $14_1, 14_2 \ldots 14_r$, are mounted on the turntable 6, so as to be generally disposed, as shown, on the opposite side of the body to the source 9. Each crystal 14 can receive radiation via a respective collimator $15_1, 15_2 \ldots 15$ which collimates the radiation into a beam through the body. Two such beams are denoted by the reference $16_n, 16_n + 1$. In this example, the crystals 14 each comprise a scintillator crystal which gives light pulses in response to incident radiation photons. Such light pulses are conveyed from each crystal via a respective light pipe $17_1, 17_2 \ldots 17_r$ to a respective photo-multiplier $18_1, 18_2, \ldots 18_r$. The photo-multipliers 18 produce output electrical signals dependent upon the incident light from the respective cyrstals and these electrical input signals are applied via conductors $19_1, 19_2 \ldots 19_r$ to a signal processing circuit 20.

In operation, the output of each photo-multiplier is integrated for successive short intervals of time, during each of which the turntable 6 moves through only a small angle. There is thus produced for each of a series of small increments of the orbital motion of the turntable, a set of output signals from the photo-multipliers dependent on the absorption of the respective beams 16 in the body enclosed by the hose 1. The timing of the integrations is controlled by a timing circuit 21 which controls the rate of rotation of the motor 11. The processing circuit 20 is arranged to reconstruct an image of the variable absorption of the elements of the section of the body, which is traversed by the swath 10 of radiation. The circuit 20 may include a digital computer arranged to carry out image reconstruction in the manner described in the aforesaid U.S. Pat. No. 1,283,915, or in the manner described in the complete specification of our co-pending U.S. Patent Ser. No. 19,528/73. To aid in the image reconstruction, the circuit 20 may include means for sorting the output signals, which are derived in sets corresponding to the beams defined by the collimators 15, into sets corresponding to parallel beams.

In the drawing, only a small number of detectors comprising crystals 14, optical couplings 17 and photo-multipliers 18 are shown and it will be appreciated that many more such detectors will be provided in a practical apparatus. For example a hundred or more detectors may be used. The drawing, however, indicates in exaggerated fashion now, by reason of the physical size of the collimators the beams 16 are separated from each other by gaps which although traversed by the radiation do not contribute to the output signals. This leads to a reduction in the number of output signals which, for a given beam width can be used in the image reconstruction, and it therefore impairs the quality of the image reconstruction. For example, the shaped region 22 between the beams $16_n$ and $16_n+1$ makes no contribution to the output signals of the set which is derived when the turntable 6 is in the angular position shown in the drawings. There is of course a similar gap between each two adjacent beams 16. However, as will be described, the apparatus illustrated enables information to be derived from the regions such as 22 so that the effective number of readings taken through the planar slice of the body can be substantially increased whilst using the same number of detectors.

As shown on the drawings the bank of collimators 15 and crystals 14 is made slidably movable in a pair of runners 23 which are fixedly mounted on the turntable 6 and the bank can be moved linearly in the direction shown by the arrow 24 by a distance corresponding to approximately one half of the spacing of the entrance apertures of the collimators.

This linear movement can be effected in a variety of ways, but is represented as being produced by a crank 24 connected to the bank of collimator 15 by a connecting link 25, the crank being driven by a motor 26, the operation of which is timed in relation to that of the motor 11 by the control circuit 21. The photo-multipliers 18 do not take part in the "side-step" of the collimators 15 and crystals 14, and the light pipes 17 which optically couple the crystals 14 to the respective photo-multipliers 18 are sufficiently flexible to allow the side-step to occur. The linear motion of the collimator and the crystals is correlated with the rate of rotation of the turntable 6 such that the aforementioned distance of travel of the bank of detectors is achieved after 360° of rotation of the turntable 6. The full amount of linear motion of the bank 11 of detectors is achieved in one step, i.e. the member 6 rotates through 360° with the bank collimators and crystals in the position shown in the drawing and then the bank is moved linearly through a distance corresponding to one half of the collimator spacing. The turntable member 6 then rotates through a further 360° with the bank in its new position. Thereafter the banks of collimators and crystals are returned to the first mentioned position, in readiness for the start of another examination.

It will be appreciated that during the second of the two rotations, the relative positions of the beams 16 and the gap 22 are interchanged, compared with the first rotation.

During the second rotation, the output signals in the sets for corresponding angular positions are dependent upon absorption occurring in the areas which were missed by the output signals derived during the first rotation. The additional signals improve the quality of image reconstruction achieved by the circuit 20. In general the beams 16 may be wider than the gaps so that there will be some overlapping of the beams during the first and second revolutions of the turntable 6.

The side step of the collimators 15 and crystals 14 may occur after a rotation of 180°, instead of 360°. Where the step occurs at 360°, the beams during the second 180° of a complete revolution will substantially register with, though being oppositely directed from those of the first 180° rotation. However, this may be preferred, since it enables the output signals derived from the pairs of oppositely directed, but substantially registering beams, to be combined.

If the bank 11 of the detectors is to be moved linearly through the aforementioned distance after 360° of rotation of the turntable 6, then instead of imparting the complete linear motion to the bank in one step as described above, the bank can be moved linearly at a slow rate, synchronously with the rotation of member 6, and throughout the 360° of rotation thereof, so that the bank has achieved the required amount of linear motion (i.e. half the collimator spacing) at the completion of the 360° of rotation. The turntable 6 then completes a further 360° of rotation whilst the bank moves through a further distance corresponding to half the inter-detector spacing. This arrangement can be achieved by driving the crank 24 continuously from the motor 11 via a gear box which provides a large reduction in rotational speed. The same modification can of course be employed when the required amount of linear motion is completed in 180° of rotation of the turntable 6. It has been discovered that, in the arrangement in which the linear motion of the bank of collimators 15 is slow but continuous throughout a full revolution of turntable 6, the slight continuous precession of the detectors relative to the source 9 is of little consequence with regard to the determination of the aforementioned absorption (or transmission) coefficients.

In some cases only the collimators 15 may take part in the additional displacement provided each crystal can receive the radiation from its respective collimator in its different positions. On the other hand the photomultipliers and the crystals may both take part in the additional displacement. Other forms of detectors than that illustrated may also be used.

In a modification of the invention, the number of absorption readings derived per move. can be increased further by causing the bank of detectors to move linearly at a slower rate than that previously envisaged so that the bank of collimators and crystals moves through the aforementioned distance corresponding to half the inter-detector spacing in, say, four revolutions of the turntable 6. This can result in obtaining, for each angular orientation of the swath, output signals corresponding to substantially overlapping beams, which has special advantages which need not be described here. In this case, moreover, it is preferable that an apertured shutter be provided between the source 9 and the body. The shutter is moved linearly in synchronism with the linear motion of the collimators and crystals and effectively divides the sectoral swath 10 of radiation into discrete beams such as 16, which move relative to the body as the bank of collimators and crystals more. This reduces the amount of radiation to which the body is exposed.

Other embodiments of the invention will be evident to those skilled in the art, and it is not intended that the scope of the invention be limited by the preceding specific description of one embodiment of the invention, and modification thereof.

What I claim is:

1. Radiographic apparatus comprising a source of penetrating radiation arranged to project a swath of radiation across a space for location of a body to be examined, means for collimating the radiation into a set of beams with gaps between adjacent beams, detector means for detecting the respective beams and for producing output signals dependent on the radiation transmitted in said beams, means for orbiting said source, said collimating means, and said detector means in the plane of said swath, and means for additionally displacing at least said collimating means relative to the source so that the relative positions of the beams and the gaps are changed during the orbital movement.

2. Apparatus according to claim 1, in which said means for additionally displacing said collimating means is such that the additional displacement is provided by a side step of the collimating means at a particular angular displacement of the collimating means.

3. Apparatus according to claim 1 in which said means for additionally displacing the collimating means is such that the additional displacement occurs gradually during the orbital movement.

4. Apparatus according to claim 1 in which said means for additionally displacing the collimating means is such that the beams and gaps are interchanged after an orbital movement of 180° or a multiple thereof.

5. Apparatus according to claim 1 in which the beams are at least as wide as the gaps.

6. Apparatus according to claim 1 in which the widths of the beams and the gaps and the additional movement are all such that the effect of substantially overlapping beams is produced.

7. Apparatus according to claim 1 in which said detector means comprise a set of scintillators which produces light pulses in response to incident radiation photons and respective photo-sensitive devices for producing an electrical output in response to said light pulses, and wherein said scintillators, but not said devices are arranged to undergo said additional displacement, the scintillator being optically coupled to the respective devices in such a way that displacement of scintillators relative to the devices can occur.

8. Apparatus according to claim 1, in which said source is arranged to produce a sectoral swath of radiation.

* * * * *

UNITED STATES PATENT OFFICE
CERTIFICATE OF CORRECTION

PATENT NO. : 3,934,142
DATED : January 20, 1976
INVENTOR(S) : Godfrey Newbold Hounsfield It is certified that error appears in the above-identified patent and that said Letters Patent are hereby corrected as shown below:

Column 3, lines 13-14, change "U.S. Patent Ser. No. 19,258/73" to --U.S. Patent No. 3,924,129--.

Column 4, line 62, change "move." to --detector--.

Signed and Sealed this

Twenty-first Day of September 1976

[SEAL]

Attest:

RUTH C. MASON
Attesting Officer

C. MARSHALL DANN
Commissioner of Patents and Trademarks